US007956086B2

(12) United States Patent
Ellis et al.

(10) Patent No.: US 7,956,086 B2
(45) Date of Patent: **\*Jun. 7, 2011**

(54) METHODS FOR THE FORMULATION AND MANUFACTURE OF ARTESUNIC ACID FOR INJECTION

(75) Inventors: William Y. Ellis, Laurel, MD (US); Peter Lim, Palo Alto, CA (US); Manaj Maniar, Freemont, CA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/658,229

(22) Filed: Feb. 4, 2010

(65) Prior Publication Data

US 2010/0184846 A1 Jul. 22, 2010

Related U.S. Application Data

(63) Continuation of application No. 12/315,209, filed on Dec. 1, 2008, now Pat. No. 7,678,828, which is a continuation of application No. PCT/US2007/013781, filed on Jun. 12, 2007.

(60) Provisional application No. 60/813,288, filed on Jun. 13, 2006.

(51) Int. Cl.
*A61K 31/335* (2006.01)
*A61K 33/00* (2006.01)

(52) U.S. Cl. ........................................ 514/450; 424/600

(58) Field of Classification Search .................. 514/450; 424/600
See application file for complete search history.

(56) References Cited

U.S. PATENT DOCUMENTS 7,678,828 B2 * 3/2010 Ellis et al. ..................... 514/450
2003/0203875 A1 10/2003 Hartell et al.

OTHER PUBLICATIONS

Ashley et al., "Malaria" Travel Medicine and Infectious Disease, Elsevier, vol. 4, No. 3-4, May 2006 pp. 159-173.
Hin et al., "Comparative pharmacokinetics of intramuscular artesunate and artemether in patients with severe falciparum malaria", Antimicrobial Agents And Cemotherapy, vol. 48, No. 11, Nov. 2004, pp. 4234-4239.
Nealon, Claire, et al.: "Intramuscular bioavailability and clinical efficacy of artesunate in gabonese children with severe malaria." Antimicrobial Agents and Chemotherapy Dec. 2002, vol. 46, No. 12, Dec. 2002, pp. 3933-3939.
Ilett Kenneth et al.: "The pharmacokinetic properties of intramuscular artesunate and rectal dihydroartemisinin in uncomplicated falciparum malaria", British Journal of Clinical Pharmacology, vol. 53, No. 1, Jan. 2002, pp. 23-30.

* cited by examiner

*Primary Examiner* — Raymond J Henley, III
(74) *Attorney, Agent, or Firm* — Elizabeth Arwine

(57) ABSTRACT

A method for the manufacture of a sterile intravenous or intramuscular formulation of artesunic acid and the formulation are the subject of this invention. First the artesunic acid powder is sterilized with ethylene oxide and placed into a sterile container. The contained sterilized powder is then dissolved in sterile sodium phosphate buffered solution to produce an injectable intravenous or intramuscular formulation. The sodium phosphate dissolves and dilutes the artesunic acid powder without caking or frothing resulting in an improved drug product. The invention also relates to the formulation and a method of treating a patient with either uncomplicated or severe and complicated malaria.

11 Claims, 2 Drawing Sheets

US 7,956,086 B2

METHODS FOR THE FORMULATION AND MANUFACTURE OF ARTESUNIC ACID FOR INJECTION

This application claims priority and is a continuation of Ser. No. 12/315,209 Filed Dec. 1, 2008, now U.S. Pat. No. 7,678,828 which is a continuation of PCT application serial number PCT/US2007/013781 filed 12 Jun. 2007, which claims priority of U.S. provisional application Ser. No. 60/813,288 filed 13 Jun. 2006.

GOVERNMENT INTEREST

The invention described herein may be manufactured, used and licensed by or for the U.S. Government.

BACKGROUND OF THE INVENTION

1. Field of the Invention

The methods of the present invention provide a unique and superior formulation of artesunic acid for parenteral injection and for the manufacture of the formulation under sterile conditions. The methods described herein provide a demonstrably sterile, non-pyrogenic product which dissolves rapidly with no frothing or caking, yielding a clear, conveniently prepared solution the attending physician may administer with confidence. The formulation that is prepared by the methods of the invention is especially suitable for the treatment of severe and complicated malaria.

2. Brief Description of Related Art

Although malaria affects about 250 million people and kills one to two million children each year, the pharmaceutical industry has shown little interest in developing new or manufacturing established antimalarial drugs not only because risks are significant, but the returns on investment are so low.

Currently, the most promising and most rapidly acting antimalarial drugs are derivatives of artemisinin (qinghaosu) obtained from qinghao or sweet wormwood (*Artemesia annua*); these drugs have been developed and manufactured in China. Three compounds of the qinghao family have been used: the parent artemisinin and two of its more-active derivatives: a water-soluble hemisuccinate, artesunate (AS), and an oil-soluble ether, artemether (AM). Both derivatives are metabolized to a common biologically active metabolite, dihydroartemisinin (DHA). Although this facile conversion (hydrolysis) to DHA contributes to the AS rapid antimalarial activity, it also limits the choices of practical AS dosage formulations.

Artesunic acid is also known to be effective in the treatment of severe (neuropathic) malaria, *Artesunate versus quinine for treatment of severe falciparum malaria; a randomized trial*, Dondorp, et al; Lancet, vol. 366, pages 717-725, Aug. 27, 2005, incorporated herein in its entirely by reference. However, Artesunic Acid is an intrinsically unstable compound, susceptible to decomposition by heat, radiation, and virtually any aqueous solution. Prior studies have confirmed the breakdown of artesunate in aqueous solutions.

AS has been used for injection with good results. However, there are drawbacks of the current commercially available AS dosage form. It is a two-component product consisting of a dry-fill powder of sterile artesunic acid in a vial and a sterile 5% sodium bicarbonate solution in an ampoule. This product, "Artesunate For Injection", is manufactured by Guilin Pharmaceutical Factory, Guangxi, China. This presently used formulation, when dissolved in the supplied bicarbonate buffer solution, results in fizzing and incomplete solution so that the concentration (dose) to be delivered may be uncertain.

The formulation of artesunic acid mentioned above is manufactured in China, and prepared by an undivulged method which results in a product of poor dissolution characteristics, and which froths and cakes upon introduction of the dissolution medium (5% bicarbonate). As the AS dissolves, carbon dioxide is evolved and trapped in the small volume of the closed vial. The formed gas bubbles carry un-dissolved AS particles throughout the vial, thereby reducing contact between these particles and the dissolution medium and lengthening the time needed to completely dissolve the AS. Moreover, this phenomenon reduces the investigator's ability to see if the solution is complete so the next preparation step, which is to dilute the AS/bicarbonate solution with 5 mL of sterile 5% glucose solution, can begin. These delays can unduly lengthen the overall solution preparation time, resulting in a shorter time period over which the prepared solution can be administered.

Further and most importantly, the product coming from China is not manufactured under the U.S. Food and Drug Administration's current Good Manufacturing Practice (cGMP).

Therefore, it is an object of the present invention to provide an AS product and a method for preparing an AS product that dissolves quickly, thoroughly and does not cake or fizz upon dissolution.

It is another object of the present invention to prepare an AS product that does not require an additional step of diluting with glucose and is immediately usable upon dissolution.

Another object of the present invention is to develop a method for the production of an artesunic acid solution for the intravenous or intramuscular treatment of malaria that is sterile and manufactured under current Good Manufacturing Practice (cGMP) as required by the U.S. Food and Drug Administration.

Another object of the present invention is to sterilize artesunic acid powder without decomposition.

Another object of the invention is to prepare an artesunic acid product that has a shelf life of two years.

These and other objects will become apparent upon further reading of this application.

SUMMARY OF THE INVENTION

The invention is a method for the manufacture of an intravenous or intramuscular formulation of artesunic acid. First the artesunic acid powder is sterilized with ethylene oxide and placed into a sterile container. Nitrogen is used to purge water vapor from the container, after which the container is hermetically sealed. When used, the sterilized powder is dissolved in sterile sodium phosphate buffered solution to produce a solution suitable for intravenous or intramuscular administration. The sodium phosphate buffered solution dissolves the artesunic acid powder without caking or frothing, resulting in an improved drug product. The invention also relates to the formulation and a method of treating a patient with severe and complicated malaria.

DETAILED DESCRIPTION

The AS parenteral dosage form must be sterile and not produce $CO_2$ when the AS dissolves. To avoid $CO_2$ evolution, we used a non-carbonate-containing, physiologically compatible basic medium. We also manufactured our drug product under cGMP.

Dissolution Medium

The dissolution medium is sodium phosphate buffered solution.

In addition to avoiding the production of gas, the dissolution medium must rapidly dissolve the AS, produce a solution in which the dissolved AS is sufficiently stable, and yields a solution of physiologically acceptable pH and osmolality. After many trials and errors, we found that a 0.30±0.05 M, pH 8.0±0.3 sodium phosphate solution meets all of the above requirements and is preferred. Slight variations from these values are acceptable.

The solute in the dissolution medium has been identified as sodium phosphate by spectral and chromatographic evidence. The average phosphate concentration is 0.30 plus or minus 0.05 M. The average solution volume is 11.0 plus or minus 0.5 mL. The average solution pH is 8.0 plus or minus 0.3.

Preparation of the 0.30M, pH 8.0 sodium phosphate solution, following a USP procedure, was straightforward and under cGMP. Sterile phosphate solution, 0.30 M, pH 8.0, is manufactured by mixing appropriate weights of monobasic and dibasic sodium phosphate in distilled water to a molarity of 0.30 M and pH of 8.0. The phosphate solution is then sterilized by filtration through a 0.22µ filter into 20 mL vials (12.2 mL/vial). The vials are sealed and then stored at room temperature.

Sterility of the product, achieved through sterile filtration of the phosphate solution and autoclave of the filled, sealed vials, was accomplished smoothly by Afton Scientific Corporation, Charlottesville, Va. 22902. After having met USP requirements for identity of the product, product sterility, endotoxin, solution concentration, volume, pH, osmolality, and particulates, 10,900 vials of this medium were labeled Afton Batch 57804, assigned WR135946; BR18064, and designated as Component Two of our AS dosage form. The USP procedure is found in 2005 USP 28/NF 23, p 2855; Composition of Standard Buffer Solutions, incorporated herein by reference.

Active Component

The active component is Artesunic Acid (AS), 110 mg/vial, SRI Batch No. 14462-16, from SRI International, Menlo Park, Calif.

The Chemical Abstracts (CA) Index name for artesunic acid is: butanedioic Acid, [3R-(3α,5a,6,8a,9α,10α,12,12a R*)]-mono(decahydro-3,6,9-trimethyl-3,12-epoxy-12H-pyrano[4,3-j]-1,2-benzodioxepin-10-yl)ester.

Figure 1:
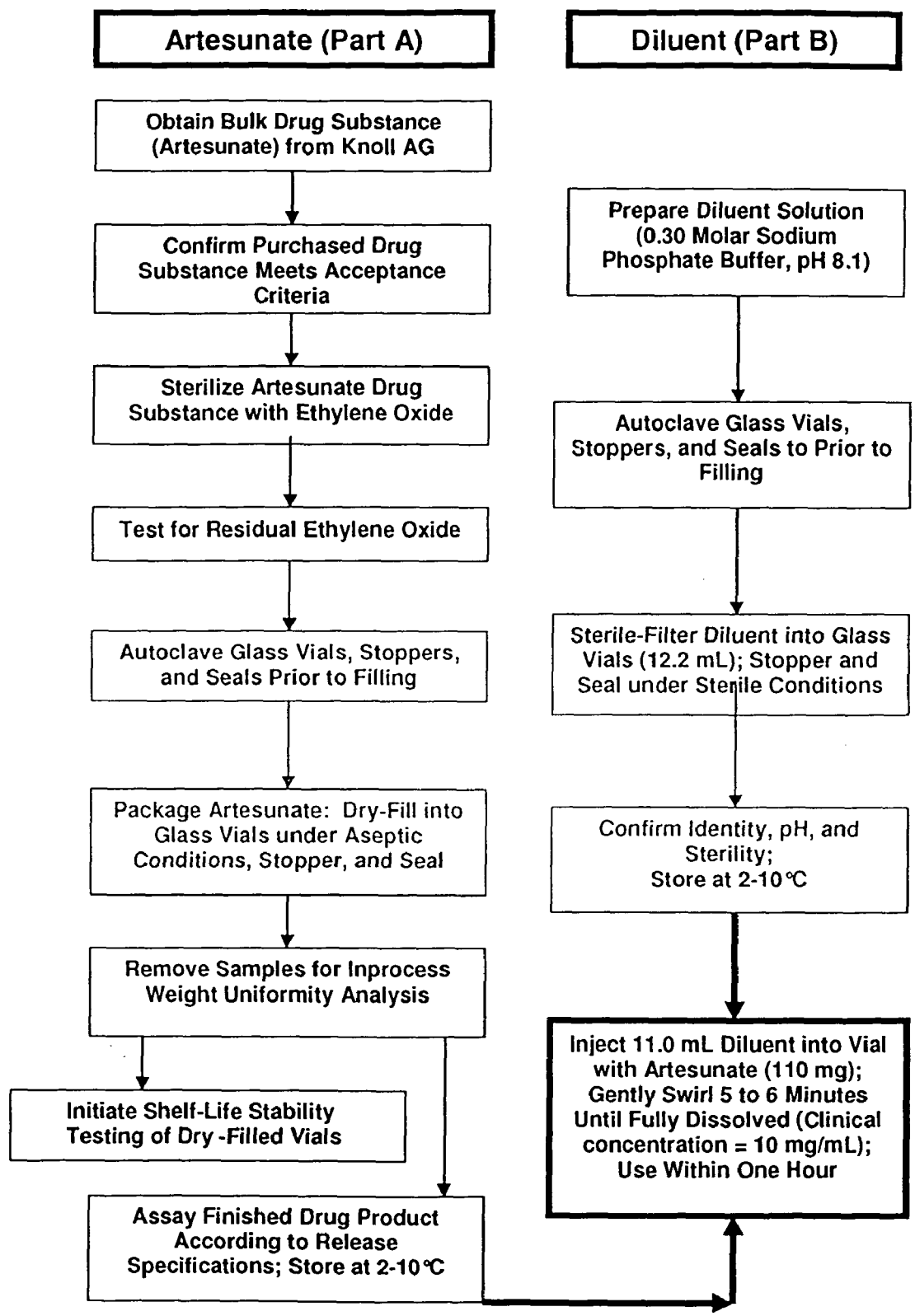
FIG. 1 is drug manufacturing flow diagram.
Figure 2:
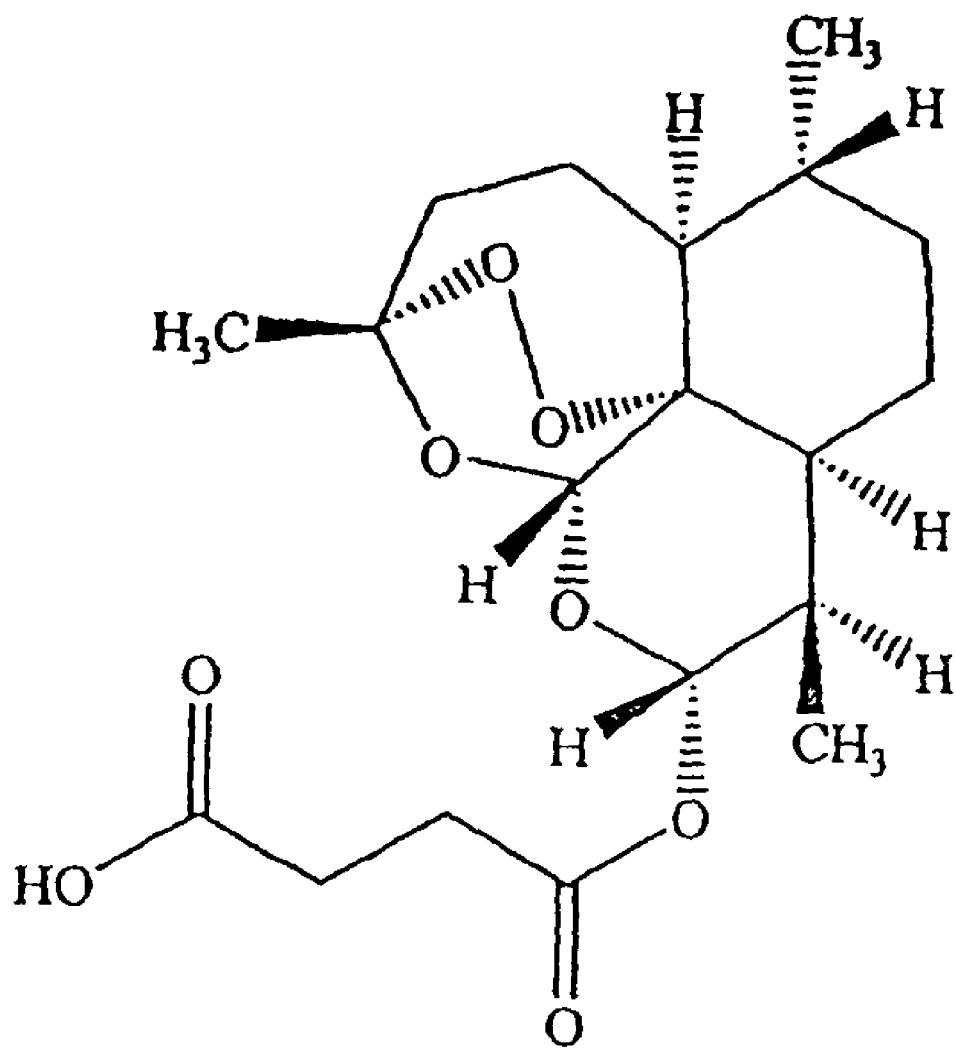
FIG. 2 is the chemical structure of α-Artesunic Acid.

The CA Registry Number is 88495-63-0, and the molecular formula is $C_{19}H_{28}O_8$. The formula weight of α-artesunic acid is 384.43 g/mol. This name also defines the stereochemistry at C-10 which, according to the CIP convention, is based on the priority of groups attached to C-10. The 10α-designation refers to the O-succinal group oriented back or toward the peroxide bridge. The 10-designation refers to the O-succinal group oriented away from the peroxide bridge. The molecular formula, $C_{19}H_{28}O_8$, corresponds to a molecular composition of C, 59.36%; H, 7.34%; and O, 33.29%; and a molecular weight of 384.43. α-Artesunic Acid is shown in FIG. 2.

The formulation development of the active component AS requires sterilization of the bulk drug. For a sterilization process to be acceptable, not only sterility of the bulk chemical must be shown, but the process must not alter the physical or chemical nature or the stability of the material. The high purity AS bulk drug, a finely milled, white crystalline powder manufactured by Knoll AG, Listal, Switzerland was used.

An acceptable EtO treatment cycle was developed and employed as follows:

Sterilization of Bulk Artesunic Acid

The bulk AS was sterilized before dry fill. Gas sterilization was used. Below are the salient points of the method and the determinations for sterility and pyrogenicity.

Artesunic Acid is treated for one hour at 102 degrees Fahrenheit and 100% humidity. The chamber is evacuated and ethylene oxide is introduced and maintained at constant pressure and 102 degrees Fahrenheit for four hours. The sterilant cycle is stopped; the chamber is evacuated and washed twice with nitrogen and once with air, all at 102 degrees Fahrenheit. Slight variations of this sterilization method are possible.

A sample of treated AS is chromatographed. Chromatograms for both treated and untreated AS are identical. AS is stable under the conditions of treatment.

Samples are tested for residual ethylene oxide, ethylene chlorohydrin and ethylene glycol. Neither ethylene chlorohydrin nor ethylene glycol was detected. Ethylene oxide was detected but at levels well below the FDA proposed limit.

A microbial limits test was performed and validated to determine the inhibitory properties of AS. The test was negative. AS has no inhibitory properties in this test. (USP 27 <61> & <71>).

Sterility tests were performed to discover the possible presence of bacteria, fungi, and spores. Samples were doped before treatment with a spore strip, bacteria, and fungi. No colony forming units were found in any test. The treated material is sterile. (USP 27 <71>).

The Limulus Amebocyte Lysate test was performed to determine the endotoxin levels in the treated AS. Endotoxin levels were below the detectable level in the to treated AS. (USP 27 <85>)

Ethylene oxide is an effective sterilant for bulk artesunic acid. Results from validated sterility tests on sterilized artesunic acid meet USP requirements for sterility testing. Sterilized artesunic acid also meets USP requirements for endotoxins.

The EtO-treated AS was dry filled into sterile vials. The best mode for this purpose was to use a portable, manually operated powder dispensing machine was purchased from M&O Perry Industries, Corona, Calif. 92880. Owing to the propensity of the AS bulk drug to clump and cling to the metal surface of the machine, characteristics that prevent both complete filling and complete discharge of the machine loads, the machine was fitted with a plastic liner that reduced the clinging and enabled quantitative discharges. The installation qualification (IQ)/operation qualification (OQ)/and performance qualification (PQ) were performed to qualify the filling machine for cGMP manufacturing. The Model LM-14 is a compact, portable bench top unit complete with carrying handle. It is an ideal machine for small fill weight, low volume applications. Other filling machines exist which are suitable for large operations.

Pre-cleaned and sterilized 20-mL vials, sterilized gray butyl rubber stoppers and flip-off aluminum seals were purchased. In a class 100 room, under laminar flow, the vials were filled in a glove box with EtO-treated AS. Scheduled weight checks were performed to ensure the filled weights met specifications. The filled vials were stoppered, sealed, and tested for release. After meeting requirements for sterility, identity, purity, content uniformity, and after constitution in sodium phosphate buffer, for solution pH, osmolality, and particulate counts, 5,500 of the filled vials were labeled SRI Batch 14462-16, assigned WR256283:BR29487, and designated as Component One of our AS dosage form.

| \multicolumn{3}{c}{Analytical Methods of Specifications for Sterile Intravenous Artesunate (110 mg/vial)} | | |
|---|---|---|
| Tests | Analytical Methods | Specifications |
| Appearance | Visual | Fine crystalline powder |
| Color Identity | Visual | White to almost white |
| IR | Conforms to Reference Spectrum | Must comply |
| HPLC | HPLC SRI TM 1900.200 | Must comply |
| Assay (HPLC) calculated on water-free basis | HPLC | 98.0 to 102.0% |
| pH | SOP SRI 004.009 | 7.2-7.7 |
| Particulate Matter in Injections | USP 788>, small volume injections | No More Than (NMT) 6000 particles of size 10 µm/vial. NMT 600 particles of size 25 µ/vial. |
| Uniformity of Dosage Units | USP 905>, Solids in Single Unit Containers | None outside 88-132 mg/vial, RSD of 10 vials ≤6.0% in Level 1; if fail, go to Level 2. |
| Sterility | USP 71> | Sterile |
| Bacterial Endotoxins, LAL, Kinetic | USP 27 through Sup 85> | 35 EU/mL |

Placebo

The selection of a material for the AS placebo was based on a likeness in appearance and physical characteristics to that of the AS dosage form, in addition to being biologically inert. The placebo for the AS Dosage Form was Mannitol, 200 mg/vial.

A large number of possible placebos were investigated. The two final candidates were mannitol and glucose, with the former having a slight edge. Because the particle size of the commercially available USP mannitol was larger than that of the AS bulk drug, the mannitol was milled and sieved to match the size and appearance of the AS powder prior to sterilization. Sterilization by irradiation initially looked promising, but after two weeks on the shelf the irradiated mannitol became discolored. Ultimately, treatment with EtO proved successful, and the sterilized mannitol was dry-filled into the same type of glass vials as the active material and processed identically. Because the density of our mannitol was nearly twice that of the AS bulk drug, the filled placebo mass was nearly twice that of the active, to maintain comparable filled volumes. After having met requirements on content uniformity, identity, and purity, and after constitution with phosphate, for solution pH, osmolality, and particulate counts, 2,500 vials of the placebo were labeled SRI Batch 14462-28 and designated WR016506:BR29487. To maintain anonymity, a common label, identifying both the AS and Placebo, was used for vials of the active as well as vials of its placebo.

In Phase I clinical trials the placebo was ethylene oxide treated mannitol, exhibiting the same appearance and dissolution characteristics as the Active Pharmaceutical Ingredient (API). The placebo was manufactured by SRI International. All clinical materials are stored, maintained, and shipped by the repository contractor (monitored and managed by The Department of Chemical Information). The repository contractor also prepares the double-blinded samples of artesunic acid or placebo for clinical use under guidance from the Department of Chemical Information. The placebo has provided an acceptable control for the recently completed phase I clinical trials.

| \multicolumn{3}{c}{Analytical Methods and Specifications for Sterile Placebo for Injection (200 mg/vial)} | | |
|---|---|---|
| Test | Analytical Methods | Specifications |
| Appearance | Visual | Fine crystalline powder |
| Color | Visual | White to almost white |
| Absence of Artesunic Acid | I.R. | None detected |
| Mannitol Content | USP (Identity) | Passes |
| Ethylene Oxide Residual | USP 71> | 200 ppm |
| Ethylene Chlorohydrin Residual | NV SOP 12C-25 (ECH) | 120 ppm |
| Sterility | USP 71> | Microbial growth is not observed |
| Uniformity of Dosage Units | USP <905>, solids in Single Unit Containers | None outside 88-132 mg/vial, RSD of 10 vials ≤6.0% in Level 1; if fail, go to Level |
| Particulate Matter in Injections | USP <788> | No More Than (NMT) 6000 particles of size 10 µm/vial. NMT 600 particles of size 25 µ/vial. |

Dosage

A typical dosage of α-artesunic acid for parenteral administration is 10 mg/mL for a 10 mL injection. 110 mg is the unit dose for manufacture. Typically, using a sterile syringe, 11 mL of sterile Phosphate buffer for injection will be added to the 110 mg artesunate vial and the vial swirled for about 4-6 minutes for full dissolution. Dosing is 1-4 mg/Kg body weight for intravenous administration with the possibility of up to 8 mg/Kg in some cases. Preferred dosing is 2-3 mg/Kg body weight for intravenous administration for three days. A drip bag is also suitable for administration of the dose. A dosage of 50 mg/mL is suitable for IM injection. IM treatment will be in the range of 1-5 mg/Kg body weight. Give dosage one to two times per day for 3 days for IM. Because the present inventors use a phosphate buffer solution, they are able to obtain a higher concentration of AS for injection than that which can be obtained with the 5% glucose dilution medium required by the Guilin formulation.

Discussion

The cGMP-manufactured α-artesunic acid parenteral dosage form of the invention offers several advantages over current, commercially available version(s) of Artesunate drug.

1. The cGMP-manufactured sterile dissolution medium, a 0.30 M, pH 8.0 solution of sodium phosphate, completely dissolves the α-artesunic acid in 2-3 min, requiring only gentle swirling. This rate of dissolution is several fold faster than that found for the Guilin product, following its directions for preparation given in its package insert.
2. Because the dissolution of AS in phosphate is not accompanied by gaseous evolution, as in the case where bicarbonate is used, determining solution completeness is readily achieved.
3. The solution prepared in phosphate is ready for administration, as no further preparation is required. The Guilin product, on the other hand, requires an additional step of dilution of the AS/bicarbonate solution with 5 mL of 5% glucose, which also must be sterile.
4. The pH of our 10 mg AS/mL solution in phosphate is 7.2, whereas that for 10 mg AS/mL solution in bicarbonate/glucose is 7.9, a solution pH that is higher than ideal for parenteral administration.
5. The osmolality of our 10 mg AS/mL solution in phosphate is 320 and that for the 10 mg AS/mL solution in bicarbonate/glucose is 410, a value also higher than ideal for parenteral administration.

6. The phosphate buffer solution of the GMP manufactured formulation allows AS concentrations high enough for effective IM treatment.

Although hydrolysis of AS in phosphate or bicarbonate/glucose begins almost immediately upon dissolution, the rates of decomposition in the two media are comparable. After two hrs at ~24° C. the solutions were still visibly clear and therefore still can be administered.

In keeping with US FDA requirements, vials of the phosphate vehicle, the AS, and the placebo are undergoing accelerated and shelf-life stability studies.

Efficacy in Trials:

An Investigational New Drug Application (IND-64769) on this drug product has been filed with the FDA and has been approved for use in clinical trials. Phase Ia Safety and Tolerance single dose clinical trials have been concluded and were successful.

Phase Ia Safety and Tolerance of GMP Formulation

Phase Ia is a single dose double-blind placebo-controlled, randomized study to evaluate the safety and tolerance of the GMP formulation of intravenous artesunate. The study has been completed successfully as is necessary to proceed to Phase IB and Phase II trials. Phase Ib and Phase II trials are in progress.

Phase Ib Safety, Tolerance and Pharmacokinetics/Pharmacodynamics of GMP Formulation A Phase 1b is a double-blind, placebo-controlled, randomized multiple dose escalation study to evaluate the safety, tolerance, and pharmacokinetics/pharmacodynamics of GMP formulation of intravenous artesunate in healthy human subjects in 3 doses using a dose escalation format using a placebo control. An objective is to determine the safety of multiple dose administration of escalating doses of artesunate that bracket the anticipated compassionate use dose of 2.4 mg/kg by measuring adverse events (AE) and cardiovascular responses (heart rate (HR), blood pressure (BP), and electrocardiogram (ECG)). Another objective is to determine the safety and tolerability of the compassionate use of 3 doses of artesunate in escalating doses of 0.5, 1.0, 2.0, 4.0, and 8.0 mg/kg with placebo control. The primary and secondary outcomes are to assess AE and hemodynamic and cardiac responses (BP,HR, ECG) and to determine pharmacokinetic parameters of artesunate and its major metabolite DHA as well as to assess preliminary dose-toxic response.

The study design is as follows: Phase I, randomized, double-blind, placebo-controlled trial using multiple ascending doses of intravenous artesunate to determine its safety, tolerability and pharmacokinetics in healthy male and female subjects. Subjects will be screened within 21 days of dosing. At the screening visit, subjects will undergo baseline VS, PE, CBC with smear, differential and indices, reticulocyte count measured by flow cytometry, haptoglobin, COAGs, Chem, UA, urine drug screen, urine HCG and medical and medication history. Eligible subjects will be scheduled for a 6-hour outpatient visit for pre-dose ECGs and VS done to approximately match dosing schedule on Day 1. On Day 0, subjects will be admitted to the CPU to begin the inpatient phase of the study. Subjects will have a brief physical and review all procedures for the inpatient stay. On Day 1, pre-dose, VS and ECG will be performed. Subjects then will receive IV study drug or placebo. Subjects will be closely monitored by evaluating hemodynamic measurements, periodic ECGs, and assessment of spontaneously reported AEs. Blood will be drawn for blood count and chemistry analysis within 12 hours of the first and last doses. PK will be drawn at designated times after each dose administered. On Days 2 and 3 subjects will receive their second and third doses, respectively, of study drug or placebo followed by close clinical monitoring and laboratory measurements as described for the first doses given. Subjects will be discharged 24 hours after the third dose of drug or placebo and followed as outpatients on Days 7, 10, and 15. The study population will consist of 40 healthy male and non-pregnant female adults given artesunate GMP manufactured for injection intravenously.

The duration of the study will be a screening of up to 21 days; 5 days (four nights) inpatient and 3 outpatient visits (last visit day 15) per patient.

Phase II Trials:

In Phase II trials, the artesunic acid parenteral dosage form of the invention was given intravenously to human subjects in Africa to treat malaria. In trials in Africa, COL Peter Weina, Chief, Department of Pharmacology, Walter Reed Army Institute of Research has reported 30 adult male and female volunteer patients with uncomplicated malaria have been successfully treated using the treatment regimen as outlined in this application. Successfully treated is defined as safely clearing *P. falciparum* malaria parasites from the blood. Patients were given a single dose of 1-4 milligrams per kilogram body weight in the form of an injection through an IV catheter (a tube with a needle attached) once a day for 3 days in a row. There were no adverse effects from the GMP IV treatment of the artesunate of the invention. The single adverse effect was with the standard-of-care positive control drug Malarone.

Stability Studies

Six thousand dry-filled vials of formulated artesunate for clinical use have been packaged. One thousand of the vials have been reserved for long-term stability testing under various conditions, including elevated temperatures and humidities, to test the integrity and durability of the packaging system. As packaged for clinical use, 20 ml vials have been dry-filled with 110 mg of ethylene oxide sterilized artesunate, stoppered, and sealed. Stability studies at Knoll have shown at least two years stability for bulk artesunic acid stored under nitrogen @ 25° C.

The sterilized bulk drug of the invention has been tested and is still undergoing stability studies. The sterilized bulk drug has shown no evidence of degradation for 20 months at 25° C. The stability studies are still ongoing.

Having generally described this invention, a Further understanding can be obtained by reference to certain specific examples which are provided herein for purposes of illustration only and are not intended to be limiting unless otherwise specified.

EXAMPLES

Example 1

GMP Formulation and Packaging

Upon receipt of the accessible portions of the European Drug Master File (DMF) for artesunic acid from Knoll, the inventors compared their analytical protocols for artesunic acid to those used in the DMF. The DMF method used by Knoll is as follows:

Validation of an HPLC-Based Assay for AS

HPLC was performed using the following conditions:

LC system

| | |
|---|---|
| Solvent Delivery | Waters 600 Pump System Controller |
| Injector | Waters 717+ Auto Sampler |
| Detector | Waters 996 Photo Diode Array (PDA) |
| Quantitation Software | Empower, Build Number 1154 |
| Method Conditions | |
| Column | YMC ODS-AQ² 250 mm Length × 4.6-mm ID, 3 μm |
| Mobile Phase | 35:65 A:B where A = 0.01M potassium dihydrogen phosphate, pH 3.8, and B = Acetonitrile |
| Flow Rate | 1.20 mL/min; pressure~2400 psig |
| Injection Size | 30-μL |
| Run Time | 20 min |
| Detection | UV @ 205 nm |

The reference solutions (n=5 each) were prepared by accurately weighing between 3.472 to 15.977 mg of the reference and dissolving each in 1.00 mL of acetonitrile. A series of 30-μL injections were made to deliver 104.2 to 479.3 μg of reference on column for assay.

Calculations (Apply to Both Reference and Sample)

The mass of sample on column ($m_x$, μg) was calculated using equation one (EQ. 1)

$$m_x = W_x \times (V_1/V_x) \quad \text{Eq. 1}$$

where, $W_x$ is the sampled mass (mg) of the reference or sample (S) as weighed, $V_x$ is the volume of solvent (1.00 mL acetonitrile) used, and $V_1$ is volume of solution injected (30 μL). An area to mass on column response factor ($RF_A$) was calculated for the reference standard using equation two (Eq. 2)

$$RF_A = (A_R/m_R) \times (100\%/P_R) \quad \text{Eq. 2}$$

Where, $A_R$ is the reference peak area, and $P_R$ is the reference purity (>99%)³. Sample peak area data was used in equation three (Eq. 3) to calculate the mass ($m_s$) of the sample, $$m_s = A_S \times (100\%/RF_A) \quad \text{Eq. 3}$$

where $A_s$ is the sample peak area.

Duplicating all the experimental conditions used by Knoll, the inventors confirmed the results of its previously validated HPLC assay. Upon validation of the imported Knoll assay, it was adopted as one of the assays to be used by the inventors to confirm the identity of artesunic acid samples and to test the purity of such samples. The major advantage of the Knoll method was lowering the LOD from 2 ug to 0.075 ug on column and decreasing the assay time from 16 minutes to 8 minutes. The major disadvantage is its inability to determine AS in phosphate. Precision, linearity, quantation, and accuracy were comparable for both methods.

The inventors verified the identity and determined the purity of three samplings of WR256283; BQ38641, (Knoll Lot 2.03). This was the milled sample of the bulk Knoll drug substance used in formulation of the injectable artesunic acid for clinical trials. The three samples were taken to confirm the identity and uniformity of the received material (Sample A from the top of the container, Sample B from the middle of the same container, and Sample C from the bottom of the container). They were compared to a reference sample received Jun. 29, 2001 (WR256283; BP18288) using a number of analytical tests including, but not limited to, Fourier Transform Infrared Spectroscopy, Proton Nuclear Magnetic Resonance Spectroscopy, Elemental Analysis, High Performance Liquid Chromatography, Thermogravimetric Analysis, Residual Solvents by Gas Chromatography, and Inductively Coupled Plasma. The samples were confirmed as being identical samples of artesunic acid. Purity was determined with an HPLC-based assay using the external standard method, with a known reference purity of >99%. HPLC results confirmed sample purity was 99.3 plus or minus 0.3%. Residual solvents in the Knoll material include heptanes (0.09%) and ethyl acetate (0.04%), plus trace amounts (<0.01%) of methanol and ethanol. Lead was not found.

SRI verified that an ethylene oxide sterilization treatment (4 hours at 102 degrees F.) does not degrade artesunate; the treated material meets USP requirements for sterility. The EtO treated sample was purged with nitrogen to remove residual ethylene oxide. Subsequently, bioburden, bacteriostasis, fungistasis, and endotoxin tests were performed to validate the sterility treatment method. Tests for ethylene oxide derivatives were negative and the residual EtO was found to be well below the FDA recommended levels. Tests for artesunate breakdown products, including dihydroartemisinin, were similarly negative. Results from validated bioburden and LAL tests on sterilized artesunate met USP requirements for sterility and endotoxins. The average chromatographic purity after ethylene oxide treatment was found to be 99.9 plus or minus 0.4% relative to the reference standard. Qualitative and quantitative assay results verified the chemical integrity of the ethylene oxide-treated artesunate. These results establish the time zero data point for future ethylene oxide-treated artesunate stability studies.

Six thousand dry-filled vials of formulated artesunic acid for clinical use have been packaged. One thousand of the vials have been reserved for long-term stability testing under various conditions, including elevated temperatures and humidities, to test the integrity and durability of the packaging system. As packaged for clinical use, 20 ml vials have been dry-filled with 110 mg of ethylene oxide sterilized artesunic acid, stoppered, and sealed. Stability studies at Knoll have shown at least two years stability for bulk artesunic acid stored under nitrogen @ 25° C.

Example 2

Preclinical Toxicology

Tests of the dry-filled artesunate formulation were used in the GLP 14-day dog toxicity study. A concentrated formulation of 50 mg AS/ml was developed and manufactured for a 14-day cGLP toxicity study in dogs. The dry-filled artesunic acid formulation used in the GLP 14-day dog toxicity study was confirmed to be of high purity by independent analysis. The artesunic acid content weights, calculated from determining the mg of artesunic acid/mL in reconstituted samples, met the requirements set forth in USP Article <905> and ranged between 501 to 519 mg/vial.

The potential toxicity of GMP artesunate of the invention was tested in beagle dogs. The artesunate was administered daily by rapid intravenous infusion (over 4 to 6 minutes) for 14 days. Four groups consisting of 4 dogs/sex/group were treated daily with doses of artesunate at 10, 20, 35, or 50 mg/kg/day at dose volumes of 1 mL/kg. One group of 4 dogs/sex received sterile 0.3 M phosphate buffer (control article) and served as the control group. The study was divided into two parts. After 14 doses, 2 dogs/sex/group were necropsied on study day (SD) 15. The remaining two dogs/sex/group were allowed a 2-week treatment-free recovery period and were necropsied on study day 29. Measurements included survival, clinical observations, body weights, electrocardiography, hematology, clinical chemistry, coagulation parameters, gross pathology, organ weights, and histopathology (Wu and Senate, 2004). Intravenous doses of artesunate up to and including 50 mg/kg/day did not result in test article-related effects on mortality, clinical observations, body weights, body weight gains, food consumption, electrocardiographic output, clinical chemistry and coagulation, gross pathology, organ weights, and histopathology. During the course of the study, erythema, diarrhea, emesis, mucoid feces, and soft feces were observed sporadically in both control and test article-treated groups, and were not considered to be test article-related. Intravenous administration of artesunate at doses of 20, 35, or 50 mg/kg/day for 14 days in beagle dogs resulted in lowered red blood cell parameters (RBC, HGB, HCT, and RETIC) measured on study day 15. The lower reticulocyte counts suggested that there was not a regenerative response to the lower RBCs. The lowered red blood cell parameters found on study day 15 were not present on study day 29.

Based on the results of this study, artesunate, when administered intravenously for 14 days at doses up to and including 50 mg/kg/day, did not result in any other test article-related adverse effects except on the measure hematology. At doses of 20 mg/kg/day and above, intravenous administration of artesunate for 14 days resulted in a transient test article-related effect on red blood cell parameters, including RBC, HGB, HCT, and RETIC.

Having now fully described the invention, it will be apparent to one of ordinary skill in the art that many changes and modifications can be made thereto without departing from the spirit or scope of the invention as set forth herein.

What is claimed is:

1. A method for the production of an artesunic acid product that has a shelf life of two years and that does not produce $CO_2$ upon dissolution comprising the steps of:
   a. sterilizing artesunic acid powder;
   b. dissolving said sterilized artesunic acid powder in physiologically acceptable buffered solution to produce an injectable formulation.

2. The method of claim 1, wherein said physiologically acceptable buffered solution is sodium phosphate.

3. The method of claim 2, wherein the sodium phosphate solution has an average of about 0.30±0.05 M, and a pH of about 8.0±0.3.

4. The method of claim 1, wherein said artesunic acid product has an osmolarity of 320 for a 10 mg/ml artesumic acid solution.

5. An artesunic acid formulation prepared by the method of claim 1.

6. A kit for making an artesunic acid formulation comprising: a first vial containing artesunic acid powder that has been sterilized with ethylene oxide and purged with nitrogen to remove water vapor and a second vial containing sodium phosphate solution of an average of about 0.30±0.05M at an average pH of about 8.0±0.3, wherein when said sodium phosphate solution is mixed with said artesunic acid in said first vial, a sterile artesunic acid solution is formed with no clumping or $CO_2$ production upon dissolution of the artesunic acid.

7. A method for treating a malaria patient comprising the steps of:
   a) preparing a formulation of sterile artesunic acid solution by the method of claim 1; and
   b) administering said sterile artesunic acid formulation to said patient by intravenous or intramuscular injection.

8. A method of preparing a single dose of artesunic acid for parenteral or intravenous administration comprising: mixing 11 mL sterile physiologically acceptable buffered solution with 110 mg artesunate.

9. The method of claim 8, wherein said physiologically acceptable buffered solution is sodium phosphate.

10. The method of claim 7, wherein said intravenous injection is via a drip bag.

11. The method of claim 8, wherein said sterile artesunic acid solution is given at a dose of 1-8 mg/Kg body weight for intravenous injection one to two times per day for three days.

* * * * *